(12) United States Patent
Astola

(10) Patent No.: US 8,382,531 B2
(45) Date of Patent: Feb. 26, 2013

(54) ELECTRICAL CONNECTOR ASSEMBLY

(75) Inventor: Pekka Simeon Astola, Espoo (FI)

(73) Assignee: General Electric Company, Schenectady, NY (US)

( * ) Notice: Subject to any disclaimer, the term of this patent is extended or adjusted under 35 U.S.C. 154(b) by 99 days.

(21) Appl. No.: 12/938,487

(22) Filed: Nov. 3, 2010

(65) Prior Publication Data

US 2011/0151728 A1 Jun. 23, 2011

(30) Foreign Application Priority Data

Dec. 22, 2009 (EP) .................................. 09180270

(51) Int. Cl.
*H01R 13/40* (2006.01)
(52) U.S. Cl. .................................................. 439/733.1
(58) Field of Classification Search ............... 439/733.1, 439/729, 857, 435, 865, 869, 874
See application file for complete search history.

(56) References Cited

U.S. PATENT DOCUMENTS

| | | | | |
|---|---|---|---|---|
| 2,291,674 A * | 8/1942 | Alden | ............................ | 439/342 |
| 3,728,669 A * | 4/1973 | Churla | ........................... | 439/859 |
| 4,040,697 A * | 8/1977 | Ramsay et al. | ................ | 439/268 |
| 4,178,052 A * | 12/1979 | Ekbom et al. | .................. | 439/268 |
| 4,220,387 A * | 9/1980 | Biche et al. | ..................... | 439/470 |
| 4,671,591 A * | 6/1987 | Archer | ........................... | 439/346 |
| 4,842,557 A * | 6/1989 | Muz | ........................... | 439/857 |
| 5,232,383 A * | 8/1993 | Barnick | ........................ | 439/859 |
| 5,944,562 A * | 8/1999 | Christensson | ................ | 439/729 |
| 5,980,337 A * | 11/1999 | Little | ................ | 439/857 |
| 6,357,089 B1 * | 3/2002 | Koguchi et al. | ................. | 24/536 |
| 6,482,050 B1 * | 11/2002 | Lemke et al. | ................. | 439/856 |
| 6,676,428 B2 * | 1/2004 | Burton | .......................... | 439/270 |
| 7,892,017 B2 * | 2/2011 | Meyer et al. | ................... | 439/435 |
| 2009/0149731 A1 | 6/2009 | Selvitelli | | |

\* cited by examiner

*Primary Examiner* — Alexander Gilman
(74) *Attorney, Agent, or Firm* — Global Patent Operation

(57) ABSTRACT

Electrical connector assembly comprising a cover part and a contact assembly for providing a mechanical and electrical contact to an electrode, and connecting arrangements for connecting lead wire to the contact component. The contact component is made of an elongated flat-formed strip forming at least two contact points for the electrode and between the contact points forming a recess having walls enlarging when drawing away from the contact points. The contact points are arranged to press against the electrode for detachable fastening.

20 Claims, 4 Drawing Sheets

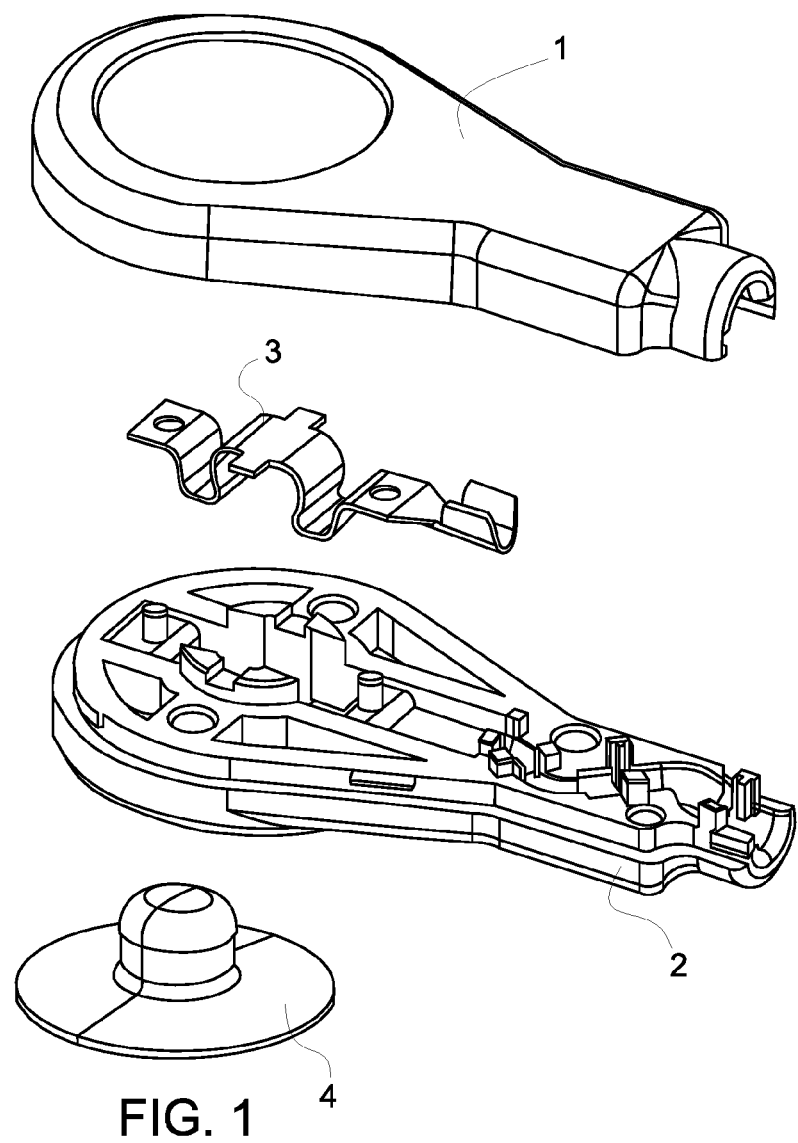
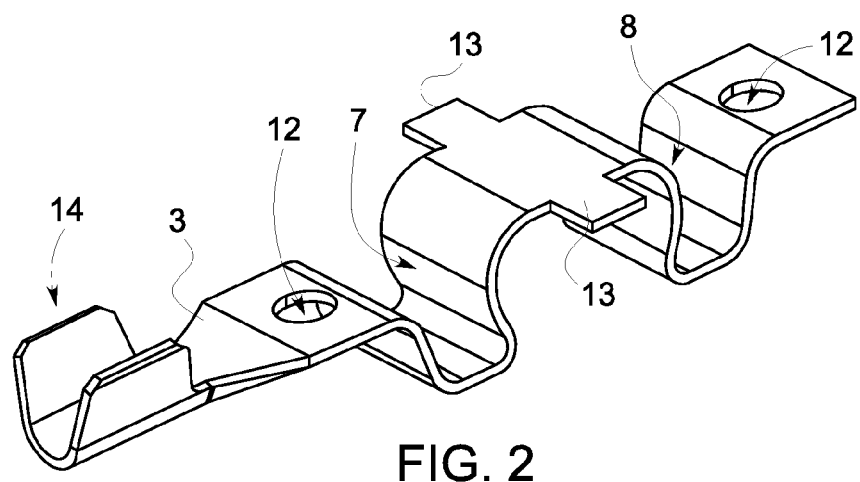

US 8,382,531 B2

ELECTRICAL CONNECTOR ASSEMBLY

BACKGROUND OF THE INVENTION

The disclosure relates to electrical connector assembly for connecting a lead wire to a press stud of a medical electrode, comprising a cover part and a contact component for providing a mechanical and electrical contact to the press stud of the patient skin electrode, and connecting arrangements for connecting lead wire to the contact component.

Electrocardiogram, ECG or EKG is a non-invasive test used to measure electrical activity in the heart. Electrocardiogram creates a graph that represents the normal phases of activation of the heart.

In electrocardiogram measurements electrical sensors called electrodes, i.e. patient skin electrodes are attached to predetermined positions on the arms, legs, and chest to record electrical activity and help assess heart function.

There is a global need to lower the costs of healthcare. This is due to the fact that average age of the whole population rises continuously, and therefore there are considerably more elder people that earlier and that is the reason why there are continuously increasing patient costs for public and private healthcare sectors.

The other need in healthcare is to reduce risk of cross-contamination between patients, for example with single patient use medical devices. These single use medical devices must be affordable to the care giver.

Owing to the facts above there is also a growing need for lowering the manufacturing costs with the electrocardiogram accessories. When carrying out efforts to lower the costs it is however extremely important simultaneously keep the reliability of the contact to the electrode in a safe level. Mechanical durability, electrical contact and signal quality must not be sacrificed during optimization efforts for costs.

Detachable connector, for example a snap connector, instead of integrated electrodes is necessary because the electrodes may need to be replaced during for example hospital stay of the patient. By replacing only the electrodes, and not the cables, total cost level of monitoring is considerably less when compared to use of integrated electrodes, i.e. technique in which also the cables must be replaced in situations when electrodes must be replaced.

Typical known prior art electrocardiograph snap connector assembly comprises a moulded plastic cover, a metallic top half, a bottom half for a spring element and a spring element for creating contact and normally further a lead wire, i.e. four or five parts if the lead wire is counted.

The number of parts lead to rather complicated and laborious manufacturing process in which there are seven cost rising manual steps, i.e.:
1. Cutting the spring wire
2. Forming the spring wire
3. Attaching the spring wire to the bottom half
4. Attaching the base and the spring to the top half
5. Preparing the lead wire, cutting and peeling of the outer and inner isolation
6. Soldering of the lead wire to the top half
7. Moulding of the plastic cover In this connection it must also be understood that soldering of the lead wire to the top half needs perfect temperature and skilled personnel leading to rising of the costs.

As described above the assemblies known from the prior art comprise numerous forms of medical clips. Said solutions are generally formed from a moulded plastic body having an embedded electrically conducting infrastructure that is exposed in a female aperture for connection to a post of a medical electrode. Electrically conductive element is usually formed from several independent metal parts which are assembled together to for a final element. Number of various parts are often considerably high in the solutions known from the prior art which increases costs of said solutions.

Increased use of electrical instrumentation in the medical field has created increasing demands for inexpensive but reliable medical terminal connector. The medical field is still today seeking to find a highly economical, reliable and secure medical terminal connector. The situation described has become even worse in the later years because the number of the elderly people rises very rapidly and economical demands are very strict today.

BRIEF DESCRIPTION OF THE INVENTION

The above-mentioned shortcomings, disadvantages and problems are addressed herein which will be understood by reading and understanding the following specification.

In one embodiment electrical connector assembly for connecting lead wire to the press stud of a medical electrode comprises a cover part and a contact component for providing a mechanical and electrical contact to a press stud of a medical electrode. The assembly comprises further connecting arrangements for connecting a lead wire to the connector assembly. The contact assembly is made of an elongated flat-formed strip forming at least two contact points to the press stud and between the contact points forming a recess having walls enlarging when drawing away from the contact points, and that the contact points are arranged to press against the press stud for detachable fastening.

In another embodiment electrical connector assembly for connecting lead wire to the press stud of a patient skin electrode, the assembly comprises a cover part and a contact component for providing a mechanical and electrical contact to the press stud of the patient skin electrode, and connecting arrangements for connecting lead wire to the contact component. The contact assembly is made of an elongated flat-formed strip forming at least two contact points for the press stud and between the contact points forming a recess having walls enlarging when drawing away from the contact points. The contact points is arranged to press against the press stud for detachable fastening.

In still another embodiment electrical connector assembly for connecting lead wire to the press stud of a patient skin electrocardiography electrode, the assembly comprises a cover part and a contact component for providing a mechanical and electrical contact to the press stud of the patient skin electrocardiography electrode, and connecting arrangements for connecting lead wire to the contact component. The contact assembly is made of an elongated flat-formed strip forming at least two contact points for the press stud and between the contact points forming a recess having walls enlarging when drawing away from the contact points. The contact points are arranged to press against the press stud for detachable fastening.

BRIEF DESCRIPTION OF THE DRAWINGS

FIG. 1 shows an explosive view of one embodiment of the contact assembly,

FIG. 2 show a detail of the embodiment shown in FIG. 1,

DETAILED DESCRIPTION OF THE INVENTION

FIG. 1 shows as an explosive view the main components of the contact assembly. In the embodiment shown there is a cover part comprising moulded top cover 1 and moulded bottom cover 2. These two parts can be attached to each other. There is also a spring element, i.e. a contact component 3. Moulded top cover 1 and moulded bottom cover 2 may be made of any appropriate material, for example plastic material. Contact component 3 may also be made of any appropriate material, for example electrically conductive and springy material, for example metal material, or alternatively of a springy material which is not electrically conductive, for example plastic material, which is provided completely or at least partially with electrically conductive coating, or electrically conductive plastic material.

FIG. 1 shows also a medical electrode 4 to which the contact component is intended to be fastened. The medical electrode 4 can be for example a patient skin electrode used in electrocardiograph measurements.

FIG. 2 shows separately the contact component 3. The particular form of the contact component is clearly shown in FIG. 2.

Figure 3:
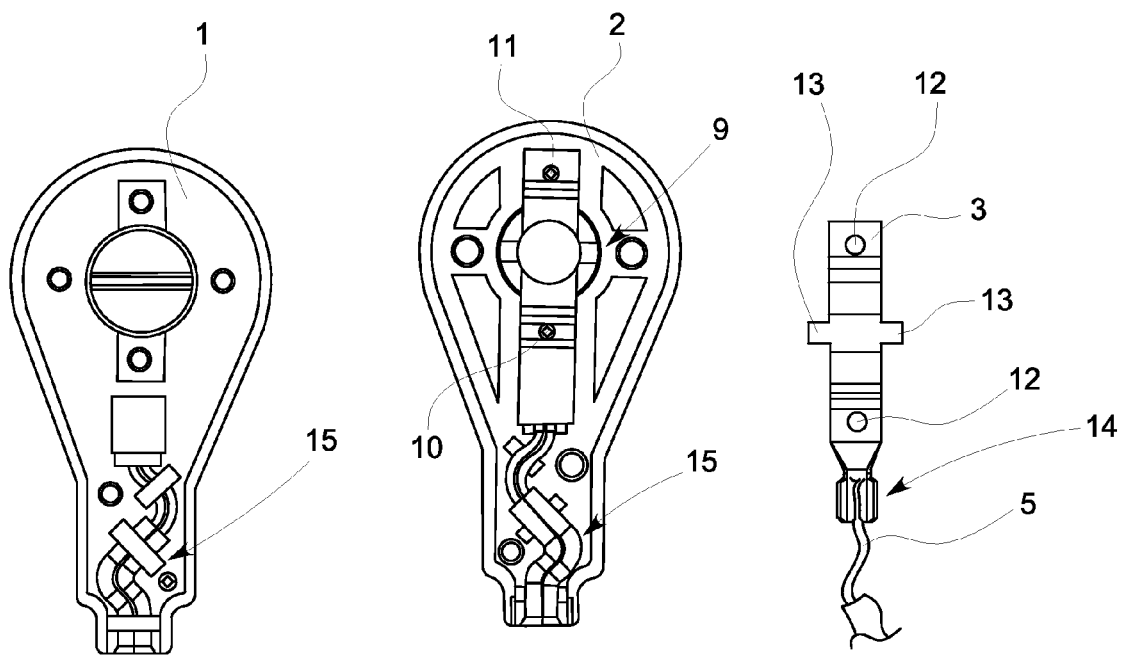
FIG. 3 shows another exploded view of the embodiment shown in FIG. 1.
Figure 4:
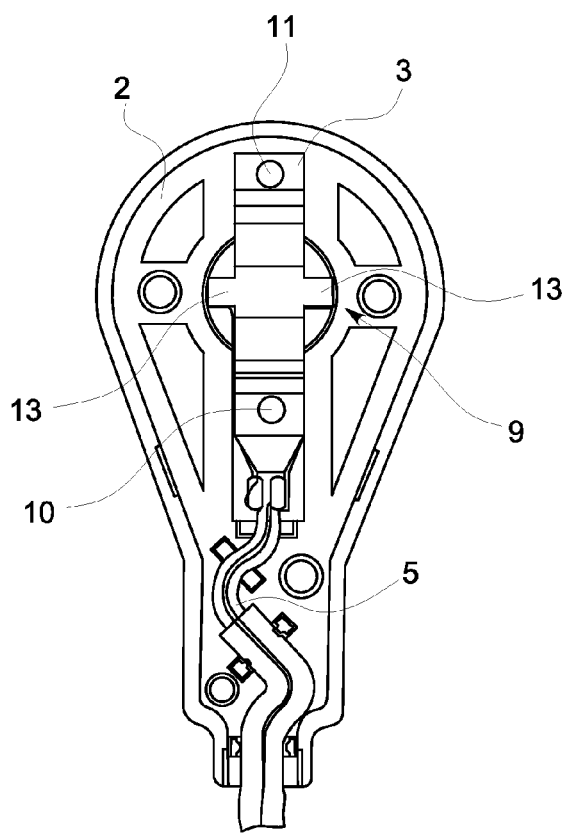
FIG. 4 shows a part of the embodiment shown in FIG. 3 in assembled form.

FIGS. 3 and 4 show the embodiment of FIG. 1 in another directions and in partially assembled form. FIGS. 3 and 4 show also a lead wire 5 connected to the connector component shown. This lead wire is intended to be used to as a conductor to feed signals from the electrode for example to electrocardiograph measuring unit. The idea and function of the lead wire is commonly known in the field and therefore said detail is not described here.

As shown in FIGS. 1-4 the contact assembly 4 is made of an elongated flat-formed strip made of for example electrically conductive material. In the embodiment shown the strip has been bent to form a recess 6. In the embodiment shown the recess have essentially U-form, or actually U-form having a widening bottom portion. Said U-form can be seen clearly for example in FIG. 2. The form of the contact component can be achieved for example by bending. The contact component is arranged to form at least two contact points A, B for the press stud. The purpose of said contact points is to create a mechanical and electrical contact to the press stud. There must be at least two mechanical contact points in order to achieve a good and reliable mechanical contact, but only one electrical contact point is needed to create a good and reliable electrical contact, i.e. for example only one of the two mechanical contact points must be provided with a conductive coating in an embodiment in which the contact component is made of electrically not-conductive material. Naturally also two electrical contact points can be used. It is further also possible to use more than two mechanical and electrical contact points for example by using a wave-formed or sawtooth surface.

Said recess is arranged to have walls 7, 8 enlarging when drawing away from the contact points. As shown in the Figures the recess 6 of the elongated flat-formed strip is formed of two walls 7, 8 placed with a distance to each other. The recess has two open sides as shown in the Figures. The walls 7, 8 discussed above form the side portions of the U-form described above. The contact points A, B are formed by said walls 7, 8. The contact points are arranged to press against the press stud for detachable fastening. The two contact points are formed by the walls 7 and 8 of the recess. The recess 6 is arranged in the two contact points to create contact forces acting in opposite directions and along the longitudinal axis of the flat-formed strip. This detail will be discussed later.

It is also possible that the bottom part of the recess 6 is arranged to form a third contact point. It is possible that the bottom part of the recess is slightly bent inwards in order to create a better contact. This is however only an alternative because said bottom part normally bends inwards when the conductor is pushed to the electrode. The recess 6 is arranged in the third contact point to create a contact force acting in right angle direction with respect to the longitudinal axis of the flat formed strip. This detail will also be discussed later.

FIGS. 1-4 show clearly that in the embodiment shown the cover part comprises at least a bottom part 2 and that the elongated flat-formed strip has been fixed to the bottom part 2. The cover part shown further comprises a top cover part 1 attachable to the bottom part 2. The cover part formed by top and bottom parts 1, 2 is provided with fastening and positioning elements 9, 10, 11 to form a press fit connection with the elongated flat-formed strip. In the embodiment shown said fastening end positioning elements are provided into bottom part 2. This is however not the only possibility but said element can also be formed into top cover part as well. The elongated flat-formed strip is provided with elements 12, 13 co-operating with the fastening and positioning elements 9, 10, 11 in the cover part.

Figure 9:
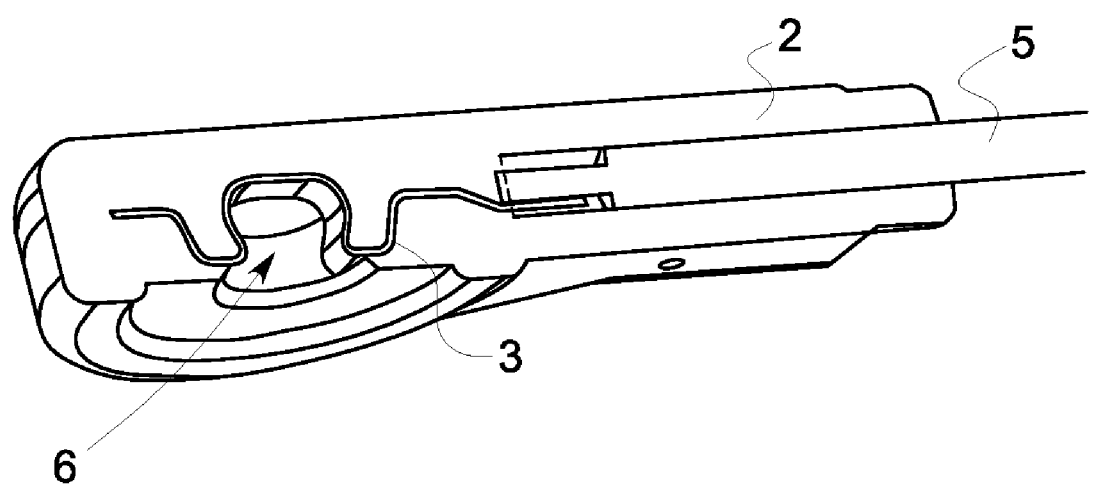
FIG. 9 shows another embodiment of the contact assembly.

As discussed above the embodiment comprises three parts, i.e. the bottom part, the contact component and the cover part. It is also quite possible that connector assembly comprises only two parts, i.e. a bottom part into which the bent elongated flat-formed strip has been fixed by moulding. FIG. 9 shows the two part embodiment described above. FIG. 9 is a longitudinal cut-away figure, i.e. FIG. 9 shows only a half of the connector so that the details inside the moulded structure can be seen.

Figures, especially FIGS. 2 and 3, show that the elongated flat-formed strip comprises connecting arrangements 14 for connecting lead wire 5 to the connector assembly. In the embodiment shown the connecting arrangements are made for press fit and is also made as an integral part of the elongated flat-formed strip. This is not however the only possibility but any appropriate connecting arrangement can be used, for example a socket arrangement into which the lead wire can be connected by using a pin-type joint element etc. It is also quite possible to use any joint elements known in the field.

Cover part may also comprise a lead wire clamp arrangement 15. In the embodiment shown the wire clamp arrangement 15 is provided into the top cover 1 and the bottom cover 2. It is however possible that the wire clamp is provided only into the part into which the bent elongated flat-formed strip has been fixed, i.e. into bottom cover 2 as shown in FIG. 2. It is also quite possible that the wire clamp can be provided into top cover 1. Hence it is possible that the wire clamp is provided into either top or bottom cover or into both.

FIGS. 5 to 8 show principally how the embodiment shown operates when used.

Figure 5:
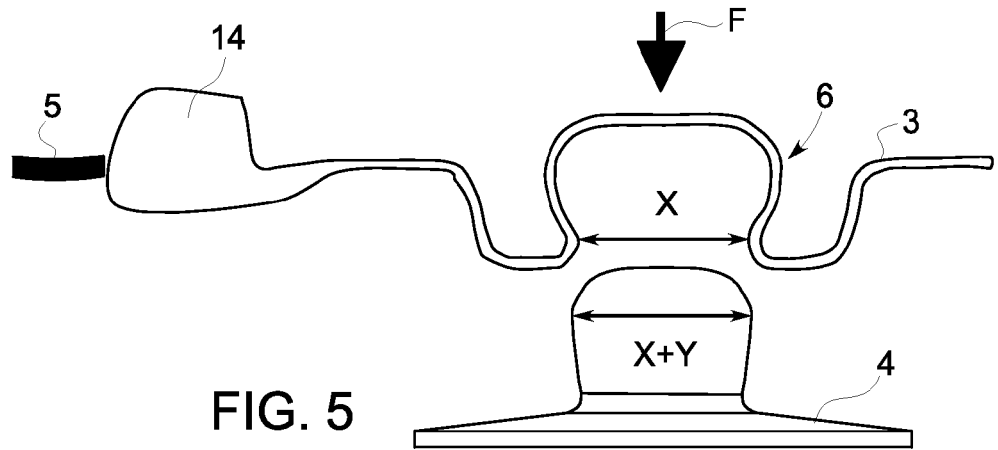
FIGS. 5 to 8 show principally the operation principle of the embodiment shown in FIGS. 1 to 4.

As shown in FIG. 5 the width X of the recess 6 has a smaller dimension than the outer diameter X+Y of the stud of the electrode 4. The width X of the recess may be for example at least 15% less than the outer diameter X+Y of the electrode stud.

Figure 6:
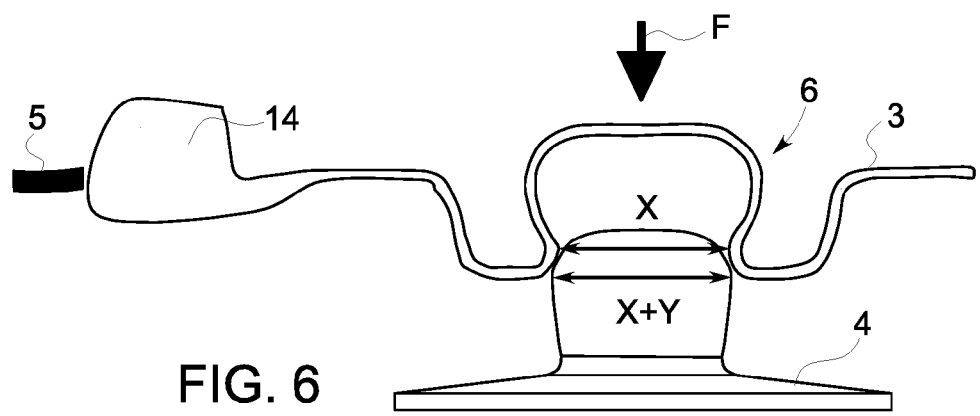
Figure 7:
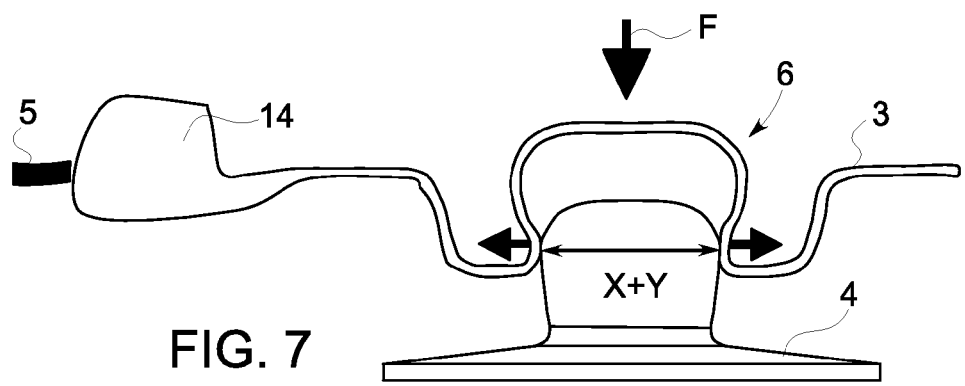
Figure 8:
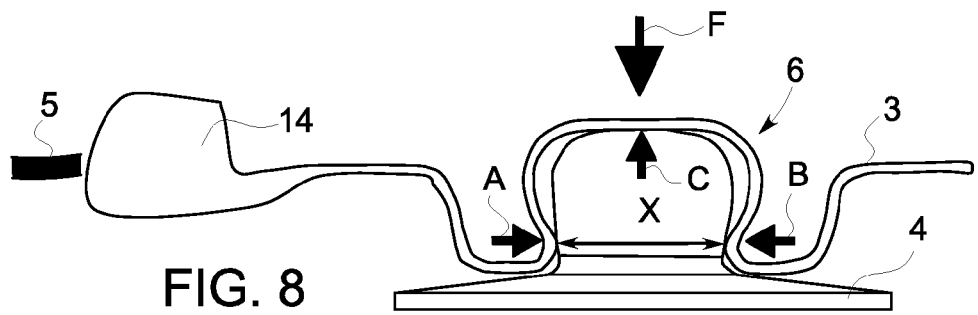

The width X of the recess 6 when pushed with a pressing force F to the stud is grown as shown in FIG. 6. As shown in FIG. 7 the width X grows symmetrically all the way to the bottom of the recess making electrical contact points at least on the side walls of the recess, i.e. in the two contact points two contact forces acting in opposite directions and along the longitudinal axis of the flat-formed strip are created as shown by the arrows A and B in FIG. 8. In practice three contact points are created because also the bottom part of the recess forms a third contact point. This is due to the fact that said bottom part bends slightly inwards when the recess is pushed to the stud. It is also possible to provide said bottom part with same inward bending in order to make the contact better. The third contact point is shown with arrow C in FIG. 8. This means that there are three contact points, i.e. from the edge areas and from the bottom area of the recess as shown in the Figures.

As discussed above and clearly shown in FIGS. 65-8 the connection obtained is fully detachable connection i.e. the connector described can be easily connected and loosened and connected again etc.

FIGS. 5 to 8 as well as FIGS. 3 and 4 show that the lead wire 5 is assembled directly to the contact component 3 made of an elongated flat-formed strip shown for example in FIG. 2. This is marked simplification when compared to the connectors of the prior art.

The embodiment discussed above uses very few components as shown for example in FIGS. 1, 3 and 4 and discussed above. This leads to rather straightforward manufacturing process with less steps when compared to the manufacturing processes of the prior art. The steps discussed above can be described principally as follows:

1. Moulding of the cover part components
2. Cutting the connector assembly (flat-formed strip)
3. Forming the connector assembly (the form shown in FIG. 2)
4. Preparing the lead wire, cutting and peeling of the outer and inner insulation
5. Attaching the lead wire to the bottom part
6. Fixing the connection assembly (flat-formed strip) to the bottom part
7. Insertion of the top part to the bottom part by using for example "click-on" joint.

The steps described above can be carried out rather easily without any need to special circumstances and highly skilled personnel. This leads to lower cost when compared to the solutions of the prior art.

This written description uses examples to disclose the invention, including the best mode, and also to enable any person skilled in the art to practice the invention, including making any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An electrical connector assembly for electrical contact to an electrode, comprising:
    a cover part; and
    a contact assembly for providing a push fit mechanical and electrical connection to the electrode; the contact assembly comprising:
        a connecting arrangement and a contact component, the connecting arrangement configured to electrically connect a lead wire to the contact component;
        the contact component comprising an elongated flat-formed strip, a bent portion with a pair of walls forming at least two contact points for detachable push fit fastening to the electrode, the pair of walls defining a recess between the contact points, the contact points being arranged to press against the electrode in a connected position and move away from the electrode during detachment, a bottom portion of the contact component connecting the walls and including a tab member for engaging a press fit connection with the cover part;
        the cover part comprising a tab member receiver for receiving the tab member of the elongated flat-formed strip and a positioning post, the positioning post configured to be received in a corresponding opening in the elongated flat-formed strip in the press fit connection.

2. The electrical connector assembly as claimed in claim 1, wherein the flat-formed strip is made of electrically conductive material.

3. The electrical connector assembly as claimed in claim 1, wherein the contact points are arranged to press against the electrode with spring properties of the elongated flat-formed strip.

4. The electrical connector assembly as claimed in claim 1, wherein the two side walls defining the recess are configured to create contact forces at each contact point acting in opposite directions and along the longitudinal axis of the flat-formed strip.

5. The electrical connector assembly as claimed in claim 1, wherein the bottom portion of the contact component is configured to form a third contact point, and the contact component is configured to create a contact force at the third contact point acting in right angle direction with respect to the longitudinal axis of the flat formed strip.

6. The electrical connector assembly as claimed in claim 5, wherein the cover part comprises only a bottom part into which the elongated flat-formed strip is fixed by moulding.

7. The electrical connector assembly as claimed in claim 5, wherein the two contact points electrically contact sides of the electrode and the third contact point electrically contacts a top of the electrode.

8. The electrical connector assembly as claimed in claim 1, wherein the cover part comprises at least a bottom part and that the elongated flat-formed strip has been fixed to the bottom part.

9. The electrical connector assembly as claimed in claim 8, wherein the cover part further comprises a top cover part attachable to the bottom part.

10. The electrical connector assembly as claimed in claim 8, wherein a wire clamp arrangement is provided at least into the bottom part.

11. The electrical connector assembly as claimed in claim 1, wherein the elongated flat-formed strip comprises connecting arrangements for connecting a lead wire to the connector assembly.

12. The electrical connector assembly as claimed in claim 11, wherein the connecting arrangements for connecting the lead wire to the connector assembly is an integral part of the elongated flat-formed strip.

13. The electrical connector assembly as claimed in claim 11, wherein the cover part is further provided with a lead wire clamp arrangement.

14. An electrical connector assembly for connecting a lead wire to a press stud of a patient skin electrode, the connector assembly comprising a cover part and a contact component for providing a push-fit mechanical and electrical contact to the press stud of the patient skin electrode, and a connecting arrangement for connecting a lead wire to the contact component, the contact component comprising an elongated flat-formed strip having a bent portion with a pair of walls forming at least two contact points for the press stud, the pair of walls defining a recess between the contact points, the walls configured to draw away from the contact points during detachment from the press stud, and press against the press stud when connected, a bottom portion connecting the pair of walls, the bottom portion having a tab member for engaging a press fit connection with the cover part, the cover part comprising a tab member receiver for receiving the tab member of the elongated flat-formed strip and a positioning post, the positioning post configured to be received in a corresponding opening in the elongated flat-formed strip in the press fit connection.

15. The electrical connector assembly as claimed in claim 14, wherein the two walls defining the recess are placed at a distance to each other, the contact points being formed by the walls.

16. The electrical connector assembly as claimed in claim 14, wherein bottom part of the recess is configured to form a third contact point.

17. The electrical connector assembly as claimed in claim 16, wherein the two contact points electrically contact sides of the press stud and the third contact point electrically contacts a top of the press stud.

18. An electrical connector assembly for connecting lead wire to a press stud of a patient skin electrocardiography electrode, comprising a cover part and a contact component for providing a mechanical and electrical contact to the press stud of the patient skin electrocardiography electrode, and connecting arrangements for connecting the lead wire to the contact component, the contact component comprising an elongated flat-formed strip forming at least two contact points for the press stud, a pair of walls forming the contact points and defining a recess between the contact points, the recess configured to enlarge when the contact component is drawn away from the press stud, the contact points being configured to engage and press against the press stud in a push-fit connection for detachable fastening.

19. The electrical connector assembly as claimed in claim 18, wherein the two walls forming the recess are placed at a distance to each other, the contact points being formed by the walls.

20. The electrical connector assembly as claimed in claim 18, wherein a bottom part of the recess is configured to form a third contact point in the push-fit connection, the third contact point being at a right angle relative to a longitudinal axis of the contact component.

* * * * *

UNITED STATES PATENT AND TRADEMARK OFFICE
CERTIFICATE OF CORRECTION

| | |
|---|---|
| PATENT NO. | : 8,382,531 B2 |
| APPLICATION NO. | : 12/938487 |
| DATED | : February 26, 2013 |
| INVENTOR(S) | : Astola |

It is certified that error appears in the above-identified patent and that said Letters Patent is hereby corrected as shown below:

In the Claims

In Column 7, Line 20, in Claim 16, delete "bottom" and insert -- a bottom --, therefor.

In Column 8, Line 1, in Claim 18, delete "lead" and insert -- a lead --, therefor.

Signed and Sealed this
Seventh Day of May, 2013

Teresa Stanek Rea
*Acting Director of the United States Patent and Trademark Office*